United States Patent [19]

Owen

[11] Patent Number: 4,824,860

[45] Date of Patent: Apr. 25, 1989

[54] TREATMENT OF PARKINSONS DISEASE

[75] Inventor: David A. A. Owen, Welwyn Garden City, England

[73] Assignee: Smith Kline & French Laboratories Limited, Welwyn Garden City, England

[21] Appl. No.: 196,653

[22] Filed: May 19, 1988

[30] Foreign Application Priority Data

May 21, 1987 [GB] United Kingdom ............... 8712073

[51] Int. Cl.$^4$ .............................................. A61K 31/40
[52] U.S. Cl. .................................................. 514/418
[58] Field of Search .......................................... 514/418

[56] References Cited

U.S. PATENT DOCUMENTS 4,452,808 6/1984 Gallagher ........................... 548/486
4,588,740 5/1986 Gallagher ........................... 548/486

FOREIGN PATENT DOCUMENTS 113964 10/1986 European Pat. Off. .

OTHER PUBLICATIONS

Chem. Abst.—105, (1986)—152924D.
Gallagher et al., *J. Med. Chem.* 28:1533, (1985).
Sulpizio et al., *Pharmacologist* 26:174, (1984).

*Primary Examiner*—Stanley J. Friedman
*Attorney, Agent, or Firm*—Stuart R. Suter; Alan D. Lourie

[57] ABSTRACT

The present invention relates to the use of certain indolone derivatives in particular, 4-(2-di-n-propyl-aminoethyl)-2-(3H)-indolone in a method of treatment of Parkinsons disease.

3 Claims, No Drawings

TREATMENT OF PARKINSONS DISEASE

The present invention relates to a method of treatment of disorders of the central nervous system, in particular Parkinsons Disease, by the administration of certain indolone derivatives.

Parkinsons Disease is a disturbance of voluntary movement in which muscles become stiff and sluggish, movement becomes clumsy and difficult and uncontrollable rhythmic twitching of groups of muscles produces characteristic shaking or tremor. The condition is believed to be caused by a degeneration of pre-synaptic dopaminergic neurones in the brain. The absence of adequate release of the chemical transmitter dopamine during neuronal activity thereby leads to the Parkinsonian symptomatology.

Currently, the most widely used treatment for Parkinsonism is administration of L-DOPA, a precursor of dopamine which acts indirectly by replacing the missing dopamine. However, disadvantages are associated with the use of L-DOPA, for example, patients often suffer from side-effects such as dyskinesia and on-off effects, and it is necessary to administer L-DOPA in conjunction with a peripheral dopa-decarboxylase inhibitor such as carbidopa or benzaseride. These inhibitors prevent the peripheral degradation of levodopa to dopamine, thus enabling more drug to enter the brain and limiting peripheral side-effects. Such treatment improves quality of life for patients but does not halt disease progression. Furthermore, such treatment is associated with a number of adverse effects including nausea, vomiting, abdominal distension and psychiatric side-effects (for example, toxic confusional states, paranoia and hallucinations).

An alternative form of therapy is to administer post-synaptic dopamine agonists, for example ergot alkaloids such as bromocriptine—however, this approach is also associated with side-effects. For example, patients receiving bromocriptine often experience dyskinesia psychiatric problems, and in a small number of cases experience vasopastic phenomena and angina. In addition bromocriptine also causes psychiatric side-effects such as hallucinations.

In view of the foregoing, it is clear that there is a continuing need for the provision of effective safe medicaments for the treatment of Parkinsonism.

It has now been found that certain indolone derivatives known in the art as pre-synaptic $D_2$-agonists having utility as cardiovascular agents (see EP No. 113964-B), also are post-synaptic $D_2$-agonists in the brain and hence are expected to have utility in the treatment of Parkinsonism.

This finding is particularly interesting since such compounds have previously been reported as not being capable of producing the central behavioural effects often seen with dopamine agonists (see Gallagher, G., Jr. et al., J. Med. Chem. 1985, 28 1533-1536). In addition, the compounds of the present invention show distinct unexpected advantages over known dopamine agonists in having been found to have additional effects on the central nervous system, namely, anti-depressant and anxiolytic effects. Furthermore, preclinical studies appear to indicate that the compounds show minimal liability to cause dyskinesia. In particular the anti-depressant and anxiolytic effects of the compounds of the present invention are perceived to be advantageous as patients receiving current therapies often also need to take separate anti-depressant medication. The presence of such qualities in a single compound may therefore reduce the need for such separate therapy.

The present invention therefore provides a method of treatment of Parkinsons Disease which comprises administering an effective non-toxic amount of a compound of structure (I)

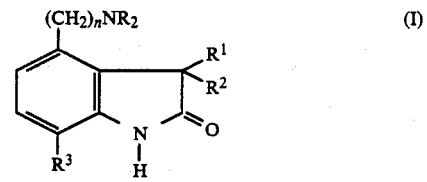

in which
each group R is hydrogen or $C_{1-4}$alkyl;
$R^1$ and $R^2$ are each hydrogen or $C_{1-4}$alkyl;
$R^3$ is hydrogen or hydroxy; and
n is 1 to 3;
or a pharmaceutically acceptable salt thereof to a subject in need thereof.

Preferably, both groups R are $C_{1-4}$alkyl in particular propyl and $R^1$ and $R^2$ are both hydrogen.

Suitably $R^3$ is hydroxy; preferably $R^3$ is hydrogen.

In particular preferred compounds for use in the method of the present invention include the compound of structure (I) in which both groups R are propyl, $R^1$, $R^2$ and $R^3$ are hydrogen and n is 2 namely, 4-(2-di-n-propylaminoethyl)-2-(3H)-indolone or a pharmaceutically acceptable salt thereof.

Suitable salts will be apparent to those skilled in the art and include, for example acid addition salts, preferably the hydrochloride.

The compounds of structure (I) and their pharmaceutically acceptable salts can be prepared by the methods described in U.S. Pat. No. 4,452,808.

In therapeutic use for the treatment of Parkinsonism, the compounds are incorporated into standard pharmaceutical compositions. They can be administered orally, parenterally, rectally or transdermally.

The compounds of structure (I) and their pharmaceutically acceptable salts which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

The compounds of structure (I) and their pharmaceutically acceptable salts which are active when administered parenterally (i.e. by injection or infusion) can be formulated as solutions or suspensions.

A composition for parenteral administration will generally consist of a solution or suspension of the active ingredient in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository composition comprises a compound of structure (I) or a pharmaceutically acceptable salt thereof which is active when administered in this way, with a binding and/or lubricating agent such as polymeric glycols, gelatins or cocoa butter or other low melting vegetable or synthetic waxes or fats.

A typical transdermal formulation comprises a conventional aqueous or non-aqueous vehicle, for example, a cream, ointment lotion or paste or in the form of a medicated plaster, patch or membrane.

Preferably the composition is in unit dose form. Each dosage unit for oral administration contains preferably from 1 to 50 mg (and for parenteral administration contains preferably from 0.1 to 15 mg) of a compound of structure (I) or a pharmaceutically acceptable salt thereof calculated as the free base.

The daily dosage regimen for an adult patient may be, for example, an oral dose of between 1 mg and 100 mg, preferably between 1 mg and 50 mg, or an intravenous, subcutaneous, or intramuscular dose of between 0.1 mg and 50 mg, preferably between 0.1 mg and 15 mg, of the compound of structure (I) or a pharmaceutically acceptable salt thereof calculated as the free base, the compound being administered 1 to 4 times per day. Suitably the compounds will be administered for a period of continuous therapy.

BIOLOGICAL DATA

Using the compound 4-(2-di-n-propylaminoethyl)-2-(3H)-indolone hydrochloride (Compound A, prepared according to procedures described in European Patent No. 113964-B) the following tests were performed:
1. Mouse spontaneous locomotor activity using individual cages equipped with photocells.
2. Mouse spontaneous locomotor activity using treadwheels.
3. Mouse spontaneous locomotor activity measuring climbing frame behaviour.
4. Measurement of stereotyped behaviour in the mouse.
5. Rat spontaneous locomotor activity using individual cages equipped with photocells: measurement of stereotypy.
6. Measurement of hyperactivity following direct administration into the mesolimbic nucleus accumbens of the rat. An indicator of anti-depressant activity.
7. Effect on observed locomotor activity following direct administration into the extrapyramidal caudate-putamen (striatum). A test for anti-Parkinsonism potential.
8. Measurement of anti-depressant activity in the mouse using the 'Porsolt Test'.
9. Anxiolytic activity in the mouse using a black and white test box.
10. MPTP-treated marmoset model. A test for anti-Parkinson activity.

A. Effect of Compound A on Spontaneous Locomotor Activity in Mice

Compound A caused inhibition of spontaneous locomotor activity in the mouse in each of the first three tests at doses of 1.0 and 10.0 mg/kg i.p. Statistically significant inhibition ($P < 0.01$—$0.001$) was measured following 10 mg/kg in test No. 1 and 1.0 mg/kg in test No. 3.

Stimulation of locomotor activity, at a statistically significant levels ($P < 0.001$), was seen after 100 mg/kg Compound A in the photocell and treadwheel tests, but not in the climbing test where the original inhibition was reversed. This biphasic activity, also exhibited by amphetamine and apomorphine in these tests, is consistent with that of a dopamine agonist having ability to stimulate presynaptic (autoreceptors) at low doses and post-synaptic receptors at a high dose. (Amphetamine is a known mood enhancer and apomorphine is a standard $D_2$ agonist of the same pharmacological class as compound A). These tests are considered to indicate dopamine agonist activity in both extrapyramidal and limbic systems.

B. Ability of Compound A to Induce Stereotypy in Rats or Mice

At doses of 1.0, 10.0 and 100 mg/kg i.p. Compound A caused no dose dependent stereotypies in the mouse or rat (tests 4 and 5). Amphetamine, at doses up to 10.0 mg/kg i.p. and apomorphine, 2.0 mg/kg s.c., produced marked stereotyped behaviour such as continuous biting, gnawing and licking in both species whereas Compound A only caused periodic sniffing.

Results

In these two tests Compound A shows a different profile to other known dopamine agonists suggesting a more selective mode of action.

C. Effect of Compound A on Locomotor Activity in the Rat

Doses of 10.0 and 100.0 mg/kg i.p. Compound A caused statistically significant ($P < 0.001$), dose-related increases in spontaneous locomotion (test 5) which lasted, at the higher dose, in excess of 2.5 hours. Enhancement of locomotor activity by amphetamine and other dopamine agonists is difficult to measure because it is complicated by the development of stereotypies. When injected directly into the mesolimbic nucleus accumbens via an indwelling cannula (test 6), Compound A (10 μg) caused a marked ($P < 0.001$) increase in spontaneous locomotion. Amphetamine, at the same dose, was equally effective, but the lower dose of Compound A (1.0 μg) was ineffective, causing a tendency to inhibition, especially during the first 10 minutes after dosing. Direct action of a compound to cause hyperactivity following administration into the mesolimbic nucleus accumbens is considered to be indicative of anti-depressant activity.

In a separate experiment, designed to measure stimulation of the striatum by recording asymmetry and circling behaviour, Compound A (0.01–10.0 μg), apomorphine (up to 50 μg) or amphetamine (up to 100 μg) were administered, unilaterally, via an indwelling cannula into the extrapyramidal caudate-putamen (text 7). Apomorphine and amphetamine were both inactive in this test but Compound A caused marked contralateral asymmetry and circling behaviour which became statistically significant at 1.0 and 10.0 μg.

Conclusion

The results from this test suggest an indication for anti-Parkinson potential for this compound.

D. Anti-Depressant Activity Using the 'Porsolt Test'

Compound A, at 0.1–10 mg/kg i/p., showed statistically significant ($P<0.05$) anti-depressant activity in mice using the Porsolt test, a test measuring the animals ability to keep stable in water. The activity was similar to that of (+) amphetamine (0.625–2.5 mg/kg i.p.) and greater than amitriptyline (2.4–40 mg/kg i.p.). The known anti-Parkinson agent Bromocriptine, 0.1–1 mg/kg i.p. caused a statistically significant reduction in swimming time at the higher dose:

Conclusion

Contrary to the effect seen in this test with the known anti-Parkinson agent bromocriptine, a compound A was found to exhibit statistically significant anti-depressant activity.

E. Anxiolytic Effect of Compound A

In a study to investigate anxiolytic acitivity in a 'Black and White' test box (test 9), Compound A (0.1–10 mg/kg i.p.) caused a statistically significant increase in the time spent in the white section and a correspondingly reduced period in the black area. This behaviour was similar to that caused by diazepam (0.125–5 mg/kg i.p.) and is consistent with other compounds having clinical anxiolytic activity. In a similar, though separate, study bromocriptine (0.1–1 mg/kg i.p.) caused a statistically significant increase in investigatory activity in the *black* area with no change in the light aversion:

Conclusion

Contrary to the effect seen in this test with the known anti-Parkinson agent bromocriptine, compound A was found to exhibit statistically significant differences in its anxiolytic effect.

F. Anti-Parkinson Activity: MPTP-Treated Marmoset Model (i) Parkinsonism-like motor deficits (hypokinesia and bradykinesia) were induced in marmosets by the intranigral infusion of 1-methyl-4-phenyl-1,2,3,6-tetrahydropyridine (MPTP) for 13 days via an implanted injection unit and osmotic minipump (Test 10). Motor deficits appeared within 3–4 days and persisted for several weeks. Drug assessments were begun after 7–10 days of infusion.

Results

Compound A (0.05–1.0 mg/kg s.c.) fully restored normal motor behaviour, although at 0.05 mg/kg, 1 or 2 marmosets did not respond:

| Behavioural measure | Control | MPTP + vehicle | Compound A (mg/kg s.c.) | | | |
|---|---|---|---|---|---|---|
| | | | 0.01 | 0.05 | 0.1 | 1.0 |
| LMA (% control) | 100 | 15 | 26 | 47*(70) | 93** | 103** |
| % time spent in LMA | 30 | 3 | 4 | 12*(23) | 29** | 28** |
| % time in head movements | 85 | 23 | 26 | 36*(80) | 83** | 84** |

LMA—Locomotor activity (movements between perch and cage floor).
Values are means (n=4); S.E.M. <13.6%, except at 0.05 mg/kg. where 1 or 2 animals did not improve (S.E.M. up to 24.2%). Values in parentheses are means from those animals responding.
Significant antagonism of MPTP impairment * $P<0.05$, ** $P<0.01$.

The most marked effect of Compound A was the full restoration of normal movements in the limbs, trunk, head and neck. In particular, characteristic rapid side to side head movements returned, as did normal facial expressions and the motor coordination for complex tasks such as jumping and playing. Furthermore, there was no development of tolerance during dosing (0.1, 1.0 mg/kg s.c.) twice daily for 7 days.

For comparative purposes tests were carried out with two known anti-Parkinson agents L-DOPA and Bromocriptine.

Treatment with L-DOPA (12.5 mg/kg i.p. 30 min. pretreatment) after benserazide (12.5 mg/kg s.c. 90 min. pretreatment) also restored MPTP-induced motor deficits, but at these relatively high doses appeared to be less effective than 0.1 mg/kg s.c. Compound A. Treatment with Bromocriptine (0.1 mg/kg s.c.) had little effect.

Conclusion

The results of this specific test confirm the potential of compound A for use as an anti-Parkinson agent.

(ii) Compound A was administered orally to MPTP treated marmosets at doses of 0.1, 0.5 or 1.0 mg/kg.

Partial reversal of the following MPTP-induced motor deficits were recorded following each dose: percentage time spent in locomotor activity, reduction in speed of head movement, reduction in speed of locomotor activity, lack of interest in surroundings, lack of facial expression, head elevation and percentage time spent in head movement. The response for the lowest dose (0.1 mg/kg, n=2) was submaximal and the highest dose (1.0 mg/kg, n=3) was supramaximal. No emesis occurred at the two lower doses.

Conclusion

The results of this specific test confirm the potential of compound A for use as an anti-Parkinson agent.

G. Receptor Binding Studies

Receptor binding studies, using rat brain, indicated that both bromocriptine and pergolide showed affinity for $5HT_1$ and $5HT_2$ receptors and pergolide also bound to dopamine $D_1$ receptors. Compound A showed no affinity for any of these receptor subtypes.

Conclusion

These studies indicate that Compound A is more selective in its binding to receptors than the other $D_2$-agonists (bromocriptine and pergolide) studied.

I claim:
1. A method of treatment of Parkinsons Disease which comprises administering an effective non-toxic amount for the treatment of Parkinsons Disease of a compound of the following structure:

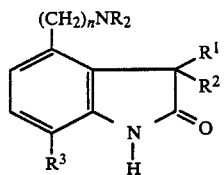

in which
each group R is hydrogen or $C_{1-4}$alkyl;
$R^1$ and $R^2$ are each hydrogen or $C_{1-4}$alkyl;
$R^3$ is hydrogen or hydroxy; and
n is 1 to 3;
or a pharmaceutically acceptable salt thereof to a subject in need thereof.

2. A method of treatment of Parkinsons Disease which comprises administering an effective non-toxic amount for the treatment of Parkinsons Disease of 4-(2-di-n-propylaminoethyl)-2-(3H)-indolone to a subject in need thereof.

3. A method of treatment of Parkinsons Disease which comprises administering an effective non-toxic amount for the treatment of Parkinsons Disease of 4-(2-di-n-propylaminoethyl)-2-(3H)-indolone hydrochloride to a subject in need thereof.

* * * * *